US00PP32198P2

(12) United States Plant Patent
Jones

(10) Patent No.: US PP32,198 P2
(45) Date of Patent: Sep. 15, 2020

(54) SWEET POTATO PLANT NAMED 'ISGLG02-1'

(50) Latin Name: *Ipomoea batatas*
Varietal Denomination: ISGLG02-1

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 0 days.

(21) Appl. No.: 16/501,766

(22) Filed: Jun. 4, 2019

(51) Int. Cl.
*A01H 5/12* (2018.01)
*A01H 6/00* (2018.01)

(52) U.S. Cl.
USPC ..... Plt./258

(58) Field of Classification Search
USPC ..... Plt./258, 263.1, 226
CPC ... A01H 5/12; A01H 5/06; A01H 5/02; A01H 5/00; A01H 5/04; A01H 6/00
See application file for complete search history.

(56) References Cited

U.S. PATENT DOCUMENTS

PP15,028 P3 * 7/2004 Pecota ..... A01H 5/06
Plt./258

OTHER PUBLICATIONS

Trademark Electronic Search System for Sweet Georgia, retrieved on Feb. 6, 2020, retrieved from the Internet at http://tmsearch.uspto.gov/bin/showfield?f=doc&state=4808:gd0q8i.2.17, one page. (Year: 2020).*

* cited by examiner

*Primary Examiner* — June Hwu
(74) *Attorney, Agent, or Firm* — Cassandra Bright

(57) ABSTRACT

A new and distinct *Ipomoea batatas* cultivar named 'ISGLG02-1' is disclosed, characterized by a vibrant light green palmate shaped foliage. Plants are upright, mounding, and outwardly spreading. Plants produce many lateral branches, without pinching or chemical growth regulators. The new cultivar is an *Ipomoea batatas*, typically suited for ornamental container and garden use.

1 Drawing Sheet

Latin name of the genus and species: *Ipomoea batatas*.
Variety denomination: 'ISGLG02-1'.

BACKGROUND OF THE INVENTION

The new variety originated as a chance discovery by the inventor, Steve Jones. The variety was discovered as a naturally occurring whole plant mutation from the unpatented commercial variety *Ipomoea batatas* SWEET GEORGIA Light Green. The new variety was discovered in August 2018 at a commercial greenhouse in Santa Paula, Calif.

After selecting and isolating the new cultivar, asexual reproduction of the new cultivar 'ISGLG02-1' was first performed by vegetative tip cuttings in a commercial greenhouse in Santa Paula, Calif. in October 2018. 'ISGLG02-1' has since produced several generations and has shown that the unique features of this cultivar are stable and reproduced true to type. Typical asexual reproduction of the new variety is by vegetative cuttings.

SUMMARY OF THE INVENTION

The cultivar 'ISGLG02-1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ISGLG02-1'. These characteristics in combination distinguish 'ISGLG02-1' as a new and distinct *Ipomoea* cultivar:

1. Great plant vigor.
2. Light green palmate-shaped foliage.
3. Upright, mounding, spreading habit.
4. Very well branched.

PARENTAL COMPARISON

Plants of the new cultivar 'ISGLG02-1' are similar to the parent in most horticultural characteristics. However, 'ISGLG02-1' differs in the following:

1. The new variety has greater plant vigor than the parent variety.

COMMERCIAL COMPARISON

Plants of the new cultivar 'ISGLG02-1' can also be compared to the commercial variety *Ipomoea batatas* 'Sweet Caroline Light Green' U.S. Plant Pat. No. 15,028. Plants of 'ISGLG02-1' are similar to plants of 'Sweet Caroline Light Green' in some horticultural characteristics, however, plants of 'ISGLG02-1' differ in the following:

1. The new variety grows more rapidly and has greater vigor than this comparator.
2. Plants of the new variety are denser and bushier with many more lateral branches, producing 15 to 25 secondary branches, compared to 14 secondary lateral branches on average of this comparator.
3. Mature upper foliage color of the new variety is Yellow-Green 145A, mature upper foliage color of this comparator is Yellow-Green 151A and 151B.

4. Mature lower foliage color of the new variety is Green 138B, mature upper foliage color of this comparator is Yellow-Green 145B.
5. The new variety does not have the characteristic anthocyanin coloration at nodes found in this comparator.

BRIEF DESCRIPTION OF THE PHOTOGRAPH

The accompanying photograph illustrates in full color a typical plant of 'ISGLG02-1' grown in a greenhouse in Santa Paula, Calif. This plant is approximately 8 weeks old, from an unrooted cutting, shown in a 1 gallon pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The R.H.S. Colour Chart, 2007, except where general terms of ordinary dictionary significance are used. The following observations and measurements describe 'ISGLG02-1' plants grown during the Spring months in a greenhouse in Santa Paula, Calif., under bright, unshaded conditions. Average day temperatures were approximately 20° C. to 26° C. and the average night temperature was approximately 15° C. to 18° C. No artificial light, photoperiodic treatments or chemical treatments were given to the plants. Measurements and numerical values represent averages of typical plant types.

Botanical classification: *Ipomoea batatas* 'ISGLG02-1'.

Age of the plant described: Approximately 8 weeks from an unrooted cutting.

Container size of the plant described: 1 gallon commercial container.

Propagation:
- *Propagation method.*—Terminal cuttings.
- *Time to develop roots suitable for transplanting.*—Summer — about 6 days at an average temperature of 24° C.; Winter — about 10 days at an average temperature of 24° C.
- *Root description.*—Thick, fleshy. Roots colored closest to RHS Yellow-White 158A.
- *Tuber description.*—Not observed to date.

Plant:
- *Growth habit.*—Upright and mounding in the center, outwardly spreading on outer circumference. Dense and bushy.
- *Height.*—Measured from top of soil line of pot, approximately 20 cm.
- *Plant spread.*—Approximately 50 cm.
- *Growth rate.*—Rapid.
- *Branching characteristics.*—Very free branching, alternate or whorled occurring.

Primary lateral branches:
- *Length.*—10 to 18 cm.
- *Diameter.*—Approximately 0.5 cm.
- *Texture.*—Glabrous.
- *Color.*—Near RHS Yellow-Green 144C.
- *Strength.*—Strong.
- *Internode length.*—0.5-1.7 cm.
- *Adventitious roots at nodes.*—Not observed.
- *Anthocyanin coloration.*—Absent.

Secondary lateral branches:
- *Length.*—Ranging from 5 to 9 cm.
- *Diameter.*—Approximately 0.4 cm.
- *Texture.*—Very slight rough pubescence.
- *Color.*—Near RHS Yellow-Green 144C.
- *Strength.*—Flexible.
- *Internode length.*—0.5 to 1.0 cm.
- *Quantity per 20 week old plant.*—Approximately 15 to 25.
- *Adventitious roots at nodes.*—Not observed.

New shoot growth characteristics:
- *Color.*—Near RHS Yellow-Green 144C.
- *Aspect.*—Upright in center of plant, outward along outer circumference.
- *Texture.*—Very slight rough pubescence.

Foliage:

Leaf:
- *Arrangement.*—Whorled and alternate, simple.
- *Average length.*—10 cm.
- *Average width.*—9 cm.
- *Shape of blade.*—Palmate with 2 very deep lobes and 2 shallow lobes.
- *Apex.*—Acute.
- *Base.*—Cordate.
- *Margin.*—Entire.
- *Aspect.*—Mostly flat, slight upward fold at mid-vein.
- *Texture of top surface.*—Glabrous.
- *Texture of bottom surface.*—Glabrous.
- *Appearance of top surface.*—Matte.
- *Appearance of bottom surface.*—Matte.
- *Quantity of leaves per lateral branch.*—Average 10 to 25.

Foliage color:
- *Young foliage upper side.*—Near RHS Yellow-Green 144B.
- *Young foliage under side.*—Near RHS Yellow-Green 145A.
- *Mature foliage upper side.*—Near RHS Green 143C.
- *Mature foliage under side.*—Near RHS Green 138B.

Venation:
- *Type.*—Palmate.
- *Venation color upper leaf.*—Near RHS Yellow-Green 144C.
- *Venation color lower leaf.*—Near RHS Yellow-Green 145C.

Petiole:
- *Length.*—Approximately 4 to 8 cm.
- *Diameter.*—Approximately 0.3 cm.
- *Texture.*—Glabrous.
- *Color.*—Near RHS Yellow-Green 145A.
- *Strength.*—Moderately strong, very flexible.
- *Aspect.*—Straight to slightly undulate.
- *Anthocyanin coloration.*—Absent to very weak. Faint coloration near Greyed-Green N189A, when present.

Flower: Flowering not observed to date.

Other characteristics:

Seeds and fruits: No seeds/fruits observed.

Disease/pest resistance: Neither resistance nor susceptibility to the normal pests and diseases of *Ipomoea* has been observed.

Temperature tolerance: Tolerates low temperatures to approximately 2° C. Good high temperature tolerance, observed to at least 40° C.

What is claimed is:

1. A new and distinct cultivar of *Ipomoea batatas* plant named 'ISGLG02-1' as herein illustrated and described.

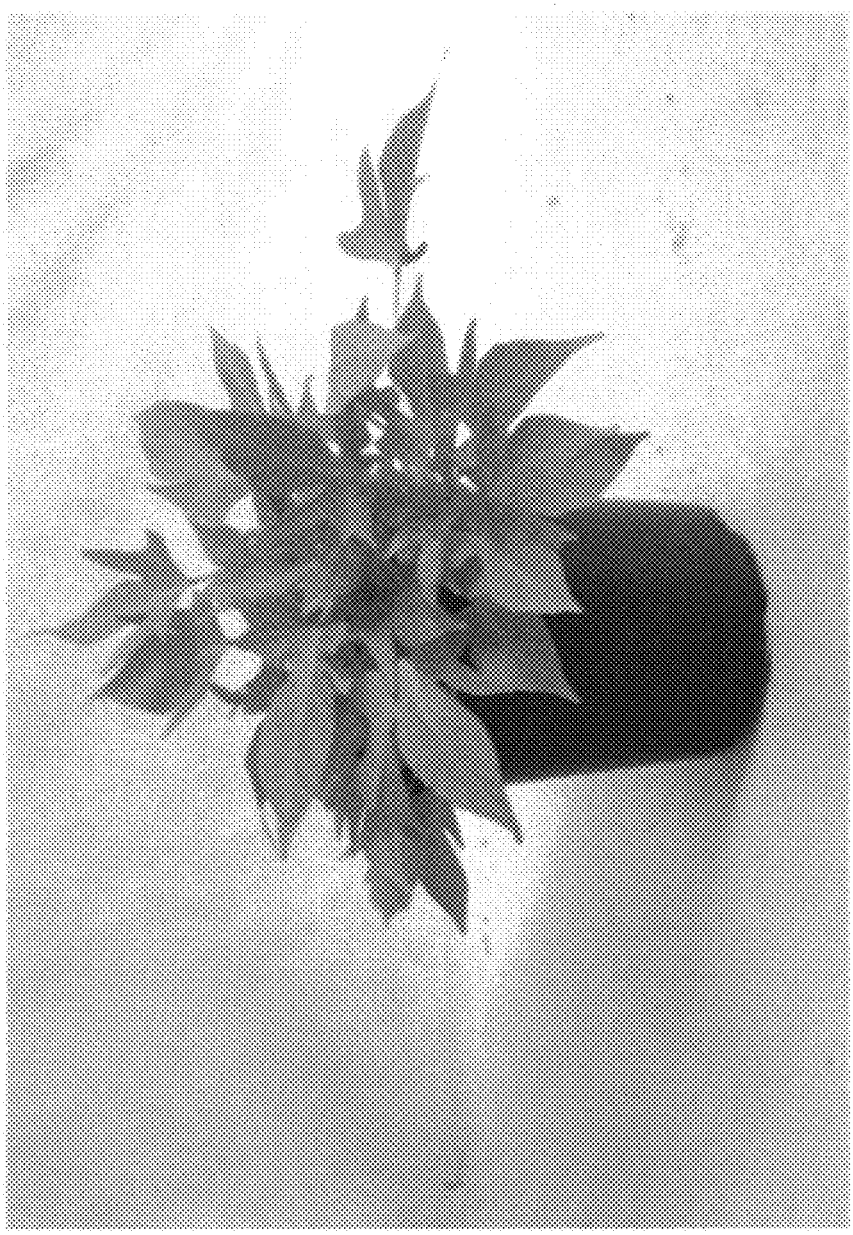

* * * * *